United States Patent
DelFavero et al.

(10) Patent No.: US 7,291,851 B2
(45) Date of Patent: Nov. 6, 2007

(54) INFRARED SOURCE MODULATION AND SYSTEM USING SAME

(75) Inventors: John R DelFavero, East Hampton, CT (US); Anthony T Pierry, Plantsville, CT (US)

(73) Assignee: RIC Investments, LLC, Wilmington, DE (US)

( * ) Notice: Subject to any disclaimer, the term of this patent is extended or adjusted under 35 U.S.C. 154(b) by 274 days.

(21) Appl. No.: 11/149,881

(22) Filed: Jun. 10, 2005

(65) Prior Publication Data

US 2005/0285055 A1    Dec. 29, 2005

Related U.S. Application Data

(60) Provisional application No. 60/583,761, filed on Jun. 29, 2004.

(51) Int. Cl.
G01N 21/61   (2006.01)
H01K 1/02    (2006.01)

(52) U.S. Cl. ............... 250/504 R; 250/343; 250/493.1; 250/494.1; 250/495.1

(58) Field of Classification Search ............. 250/504 R
See application file for complete search history.

(56) References Cited

U.S. PATENT DOCUMENTS

| | | | |
|---|---|---|---|
| 4,177,381 A | 12/1979 | McClatchie et al. | |
| 4,692,621 A | 9/1987 | Passaro et al. | |
| 4,754,141 A * | 6/1988 | Mindock | 250/343 |
| 4,914,720 A | 4/1990 | Knodle et al. | |
| 5,282,473 A | 2/1994 | Braig et al. | |
| 5,464,982 A * | 11/1995 | Drucker et al. | 250/343 |
| 5,932,877 A | 8/1999 | Braig et al. | |
| 6,023,069 A * | 2/2000 | Steinthal et al. | 250/493.1 |
| 2006/0249681 A1* | 11/2006 | Frodl | 250/343 |

* cited by examiner

*Primary Examiner*—Jack I. Berman
*Assistant Examiner*—James J Leybourne
(74) *Attorney, Agent, or Firm*—Michael W. Haas

(57) ABSTRACT

A method of modulating an infrared radiation (IR) source that includes applying a time-varying, periodic voltage signal to the IR source, measuring a parameter of the voltage signal, and adjusting the voltage signal to maintain a substantially constant delivered power to the IR source. Adjusting the voltage signal is done based on the measured parameter and a predetermined relationship between the measured parameter of the voltage pulse and a resistance of such an infrared radiation source. Alternatively, the method includes applying a the voltage pulse, measuring a first parameter of the voltage pulse and a second parameter of a current passing through the infrared radiation source resulting from the applying step, and adjusting the voltage pulse to maintain a substantially constant delivered power to the infrared radiation source based on the first parameter and the second parameter.

15 Claims, 8 Drawing Sheets

| | VOLTAGE | PULSE | PEAK T(°C) | PEAK MOD. (°C) |
|---|---|---|---|---|
| PART I | 5 | 3200 | 603.2 | 118.8 |
| | 5 | 3400 | 630.2 | 118.3 |
| | 5 | 3600 | 656.2 | 120.9 |
| | 5 | 3800 | 681.3 | 121.4 |
| | 5 | 4000 | 705.4 | 121.4 |
| PART II | 4.75 | AUTO | 604.9 | 110.4 |
| | 5 | AUTO | 604.7 | 117.8 |
| | 5.25 | AUTO | 609.1 | 125.5 |

INFRARED SOURCE MODULATION AND SYSTEM USING SAME

CROSS-REFERENCE TO RELATED APPLICATIONS

This application claims priority under 35 U.S.C. § 119(e) from provisional U.S. patent application No. 60/583,761 filed Jun. 29, 2004 the contents of which are incorporated herein by reference.

BACKGROUND OF THE INVENTION

1. Field of the Invention

The present invention relates to a system and method for maintaining a constant infrared radiation output from an infrared radiation source despite variations in a resistance of the infrared radiation source, a voltage, or a current applied to the infrared radiation source.

2. Description of the Related Art

Gas analyzers are widely used in medical applications and are typically categorized into two different types: (1) "diverting" or "sidestream" gas sampling systems; and (2) a "non-diverting" or "mainstream" gas measurement systems. A mainstream gas measurement system includes a sample cell that is disposed along the main path of a breathing circuit through which a patient's respiratory gases flow and a gas sensing system coupled to the sample cell to measure the gas constituents. A sidestream type of gas measurement system transports a portion of sampled gases from the sampling site, which is typically a breathing circuit coupled to the patient's airway or directly at the patient's airway, through a sampling tube to the sample cell, where the constituents of the gas are measured by a gas sensing system coupled to the sample cell. A gas sensing system includes the elements necessary for monitoring respiratory gases including an infrared radiation (IR) source and detector. An example of a conventional mainstream gas measurement system is shown in U.S. Pat. No. 4,914,720 issued to Knodle et al. Examples of conventional sidestream gas sampling systems are taught in U.S. Pat. No. 4,692,621 to Passaro et al.; U.S. Pat. No. 4,177,381 to McClatchie; and U.S. Pat. No. 5,282,473 and U.S. Pat. No. 5,932,877 both to Braig et al.

Of considerable importance in gas sensing systems is the infrared radiation source (also referred to as an emitter), which produces the beam of infrared radiation. In non-dispersive gas analyzers, such as disclosed in the '720 patent, the emitter has resistive ink bonded to a substrate of a material with a low thermal conductivity that is electrically-pulsed in unipolar or bipolar fashion. High intensity infrared energy is emitted from the resistive ink portion of the emitter and is either reflected by a mirror and then collimated or directly collimated by a lens. With conventional infrared sources, the applied emitter voltage (Ve) must be tightly regulated by voltage regulators to achieve a consistent source output. Voltage regulators known in the art are either of the linear or switched mode type. Linear mode voltage regulators may consume greater than 30% of the power provided to them, leaving only at most 70% of the power available for to drive the emitter. While switched mode voltage regulators may consume only 10-15% of the power provided to them, they are complex and expensive.

To further complicate matters, the resistance of the emitter is not constant in each emitter in a batch of emitters due to variances in the manufacturing processes. Manufacturers may accommodate this variation in the output of the emitter by using a larger input dynamic range for the signal receiving front end of the detector portion of the gas sensing system. Additionally, the resistances of such an emitter may slowly change over time, and, therefore, so does the infrared radiation output of that emitter. The change in the resistance of the emitter can be measured by monitoring changes in the current flowing through the emitter (Ie). As a result of these variations, if either the emitter voltage or the emitter current differed from factory calibration conditions, it was possible for the output of the gas analyzer to yield results outside of its stated specification.

Given these problems with existing infrared radiation sources, it is desirable to provide an IR source that can adapt to differences in the input driving voltage and differences in the properties of the infrared radiation source, including but not limited to changes in the IR source resistance, and, at the same time, permit the infrared radiation intensity and spectral power distribution of the infrared radiation output by the IR source to remain substantially constant. It is also desirable to provide all of the advantages of such an adaptive IR source without the need to utilize a voltage or current regulator that adds cost and complexity, and wastes power.

SUMMARY OF THE INVENTION

Accordingly, it is an object of the present invention to provide a method of modulating an infrared radiation source that overcomes the shortcomings of conventional methods of infrared radiation source modulation. This object is achieved according to the present invention by applying a time-varying, periodic voltage signal to an infrared radiation source, measuring a parameter of the voltage signal, and adjusting the voltage signal to maintain a substantially constant delivered power to such an infrared radiation source. Adjusting the voltage signal is accomplished based on the measured parameter and a predetermined relationship between the measured parameter of the voltage signal and a resistance of such an infrared radiation source.

According to a further embodiment, this object is achieved by applying a voltage pulse to an infrared radiation source, wherein the voltage pulse has a duty cycle less than 100%, measuring a first parameter of the voltage pulse, measuring a second parameter of a current passing through the infrared radiation source resulting from the applying step, and adjusting the voltage pulse to maintain a substantially constant delivered power to the infrared radiation source based on the first parameter and the second parameter.

According to yet another embodiment, the object of the invention is achieved by applying a voltage pulse to an infrared radiation source, wherein the voltage pulse has a duty cycle less than 100%, measuring a parameter of the signal developed in a reference detector in response to the infrared radiation source resulting from the applying step, and adjusting the voltage pulse to maintain constant radiated power as measured by the reference detector.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
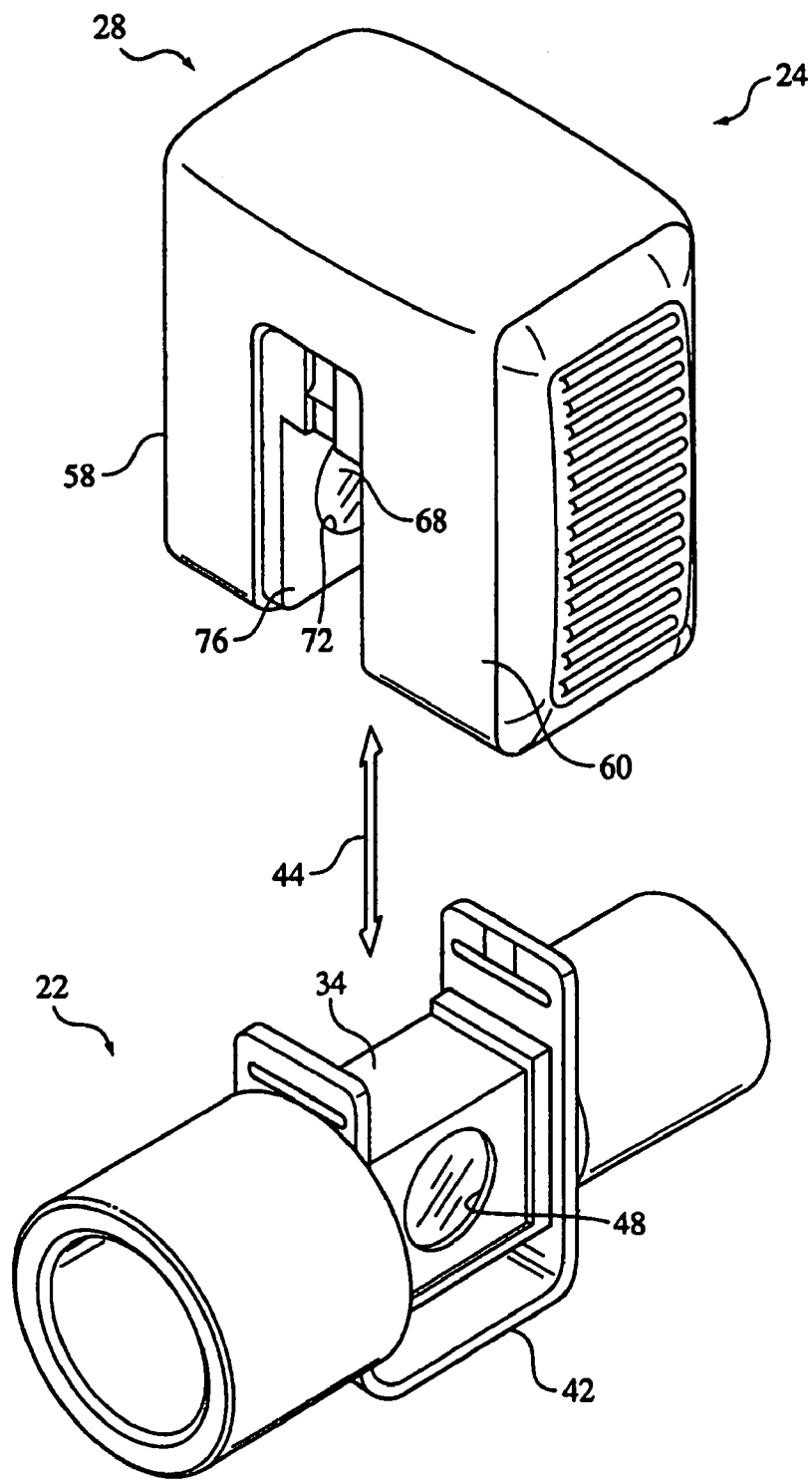
FIG. 1 is an exploded view of an airway adapter that provides a flow path for a gas being analyzed, and a mainstream gas sensing system that outputs a signal indicative of the concentration of a gas in the mixture and a reference signal.
Figure 2:
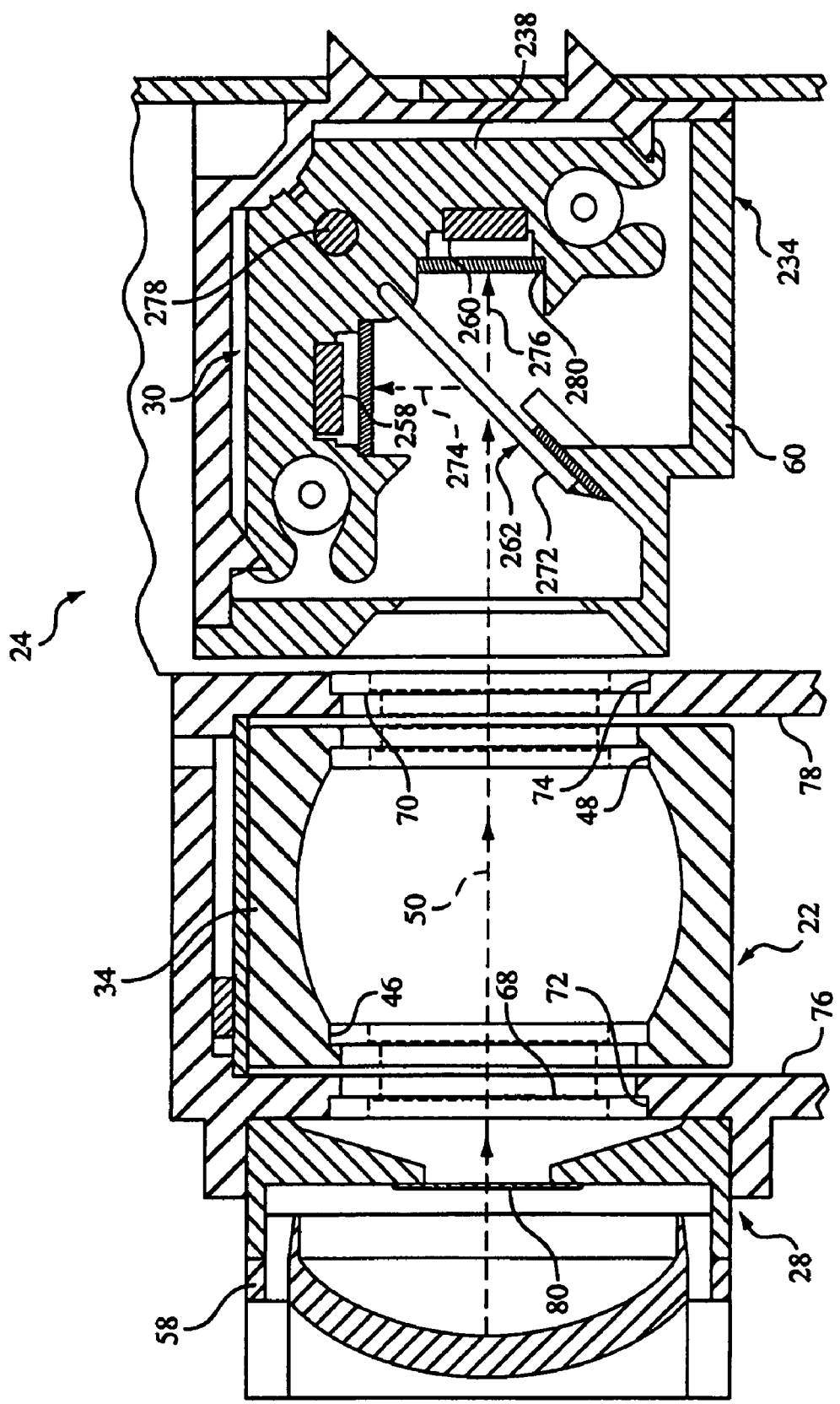
FIG. 2 is a sectional view of an optical system of in the airway adapter/mainstream gas sensing system of FIG. 1.

The present invention is applicable to both mainstream and sidestream gas sensing systems. However, for the sake of brevity, only its application with mainstream gas sensing systems will be shown and described herein. FIGS. 1 and 2 show a mainstream gas sensing system 24 that includes a housing 26 and an airway adapter 22. Housing 26 contains an infrared radiation source 28 and a detector unit 30 and is selectively mountable on a central section 34 of airway adapter 22, which provides a seat for the mainstream gas sensing system. In the illustrated exemplary embodiment, an integral, U-shaped casing element 42 positively locates mainstream gas sensing system 24 on the adapter. Arrow 44 in FIG. 1 illustrate the selective attachment and detachment of the sensing system with respect to the airway adapter.

Apertures 46 and 48 are formed in center section 34 of airway adapter 22. With mainstream gas sensing system 24 coupled to the airway adapter, these apertures are aligned along an optical path identified by reference character 50 in FIG. 2. That optical path extends from infrared radiation source 28 in transducer 24 transversely across airway adapter 22 and through the the gas(es) flowing through the airway adapter, and into an infrared radiation detector unit 30, which is disposed in a leg of the mainstream gas sensing system opposite the leg containing the IR source (i.e., the emitter).

Optically transparent windows 68 and 70 are installed along optical path 50 in apertures 72 and 74 provided in walls 76 and 78 of mainstream gas sensing system housing 26. These windows allow the beam of infrared radiation generated in IR source 28 disposed in a first section (leg) 58 of mainstream gas sensing system housing 26 to pass through airway adapter 22 and emerge from the airway adapter and pass into detector unit 30 in a second section (leg) 60 of the mainstream gas sensing system housing.

In the illustrated exemplary embodiment, detector unit 30 includes a boxlike housing 234. A monolithic, heat conductive, isothermal detector support 238 is installed in housing 234. Detectors 258 and 260 are disposed in housing 234 and are preferably made from lead selenide, because of the sensitivity which that material possesses to electromagnetic energy having wavelengths which are apt to be of interest. Detectors 258 and 260 are supported from heat conductive support 238 along with a beam splitter 272.

The beam splitter has a generally parallelepipedal configuration and is fabricated from a material such as silicon or sapphire which is essentially transparent to electromagnetic energy with wavelengths of interest. An exposed front surface 262 of the beam splitter is completely covered with a coating (not shown) capable of reflecting to data detector 258 infrared radiation impinging on the beam splitter that has a wavelength shorter than a selected value. In the illustrated exemplary embodiment of the invention, beam splitter 272 reflects to data detector 258, as indicated by arrow 274 in FIG. 2, energy having a wavelength shorter than about 4 microns. The energy of longer wavelengths is, instead, transmitted through the beam splitter to reference detector 260, as indicated by arrow 276 in the same figure. Optical bandpass filters 278 and 280 are mounted in isothermal support 238 in front of data and reference detectors 258 and 260.

Figure 3:
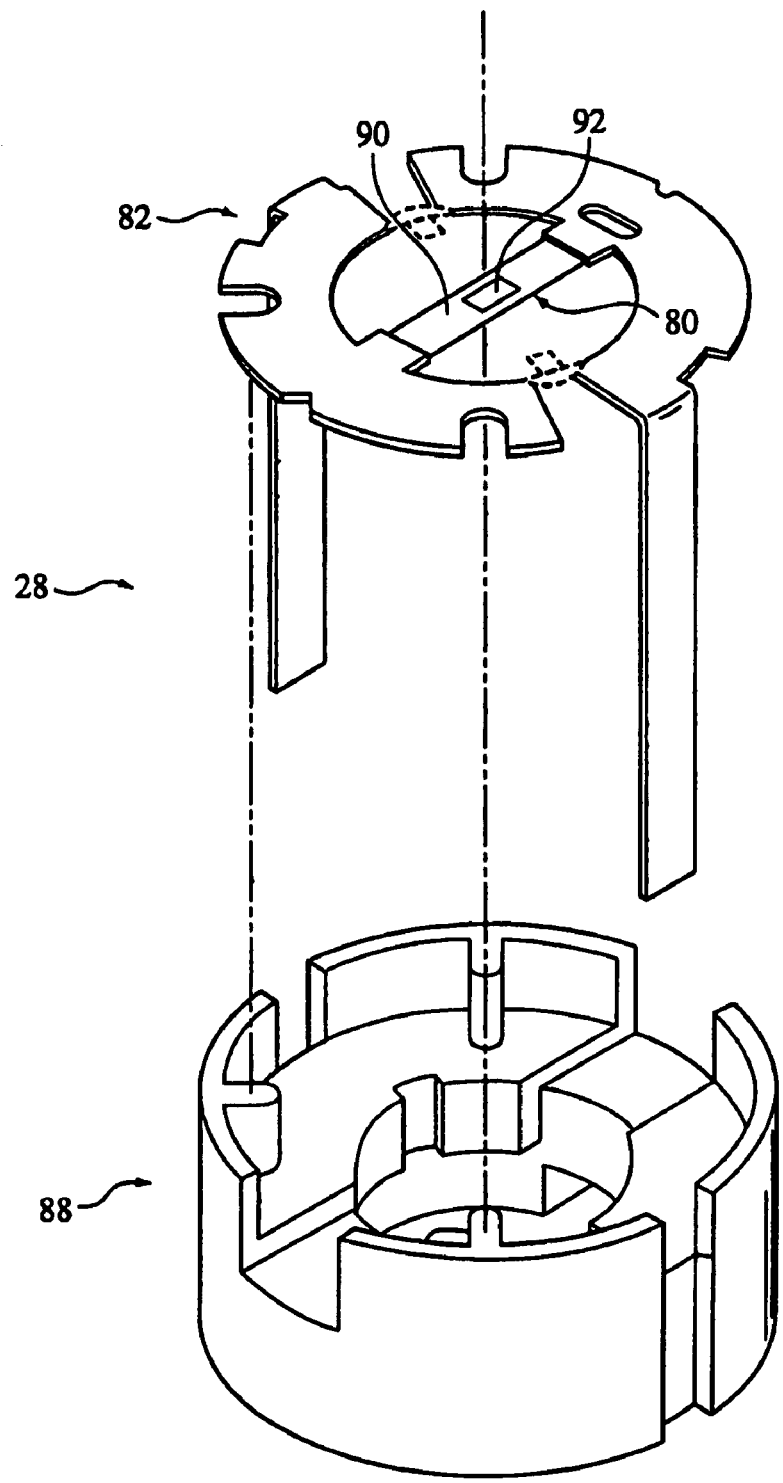
FIG. 3 is an exploded view of a frame and support ring employed to support an infrared radiation emitting element and to make electrical connections therewith.

FIG. 3 illustrates an example of infrared radiation source 28 suitable for use in first section 58 of housing 26. IR source 28 includes an thick film infrared radiation emitting element 80 mounted in a source emitter assembly 82, which is assembled with a base 88. IR source 28 includes a substrate 90, which, in one embodiment, is 0.250 inch long, 0.040 inch wide, and 0.005 inch thick. This substrate can, however, range in thickness from 0.003 to 0.005 in., and it is formed from a material having low thermal conductivity. This is important because it significantly reduces the power required to heat the emitter to its operating temperature. Infrared radiation emitting element 80 is energized to heat it to an operating temperature in which it emits infrared radiation in an appropriate range of bandwidths by effecting a flow of electrical current through an emissive layer 92 of the emitter from an appropriate power supply.

As noted above, the present invention controls or modulates the power provided to the IR source so that energy output of the IR source has a substantially constant level of modulation that can be maintained during use of the gas measurement system. This is accomplished by first understanding that the emitter includes a resistive element having a resistance Re, which is heated when power, such as an emitter voltage (Ve) at a pulse duration (width) of time Te, is applied to the emitter. Using the definition of power (Power (watts)=voltage×current) and Ohms law (Voltage=current×resistance, or Current=Voltage/Resistance), the energy applied to the emitter, for a constant rectangular wave voltage drive, can be expressed as (Ve*Ve*Te)/Re, when multiplied by time Te. The delivery of this known quantity of energy or power to the emitter will cause a temperature rise and the emission of infrared energy. The intensity spectrum of this infrared radiation, which is temperature dependent, also varies as a function of wavelength of the infrared radiation and is described by the Planck's law of black body radiation. If the voltage Ve is measured and the resistance Re known, the delivered pulsed energy, i.e., emitted modulated radiation, can be maintained substantially constant by appropriately varying the voltage, e.g., by varying the pulse width W, duration Te, pulse shape, amplitude, duty cycle, or any combination thereof. In short, the present invention contemplates any characteristic of the voltage signal applied to the IR source that impacts on the emitted radiation from the source.

As variability in the manufacturing processes yields infrared emitters with significant variation in resistance values, the resistance Re may be measured during the manufacturing process and stored for later reference. Additionally, a consideration of the present invention, is that the resistance Re is related to pulse width and that relationship is also determined during the manufacturing process and stored for later reference. Alternatively, both voltage and current could be measured during operation and the pulse width, shape, period, amplitude, or other parameter varied in an iterative fashion.

In addition to compensating for variations in the emitter resistance, the method of the present invention corrects for small variabilities in the voltage applied to the emitter, which has a magnified effect on infrared radiation output due to the non-linear relationship between emitter temperature and emitted radiation. This variability, if not corrected, would be reflected in changes in the spectral output of the infrared radiation so as to degrade the accuracy of the gas measurements.

The present invention contemplates applying a time-varying, periodic voltage signal 290 to an infrared radiation source and measuring a parameter of the voltage signal. See FIG. 7A. An example of a suitable parameter is the level of the voltage applied to the emitter. The voltage signal is adjusted to maintain a substantially constant delivered power to the infrared radiation source. Adjusting the voltage signal is accomplished based on the measured parameter and a predetermined relationship between the measured parameter of the voltage signal and a resistance of such an infrared radiation source. The predetermined relationship is, for example, the emitter voltage/resistance relationship determined for that emitter during manufacture. The present invention contemplates that adjustment of the voltage signal includes adjusting a width W of voltage signal 290, which has a period F. It is to be understood that the present invention contemplates that the adjustment of the voltage signal can be accomplished and/or described in various alternative ways. For example, width W of the voltage pulse can be described in terms of the duty cycle of the voltage signal.

A further embodiment of the present invention contemplates regulating infrared radiation output from an infrared radiation source by applying a voltage pulse to an infrared radiation source, where the voltage pulse has a duty cycle less than 100%, and measuring a first parameter of the voltage pulse. As in the previous embodiment, the first parameter is any characteristic of the voltage signal that varies with IR output of the emitter. The method further includes measuring a second parameter of a current passing through the infrared radiation source resulting from the applying step. An example of a suitable parameter of the current is the amount of current in Amps passing through the IR source. The method finally includes adjusting the voltage pulse to maintain a substantially constant delivered power to the IR source based on the first parameter and the second parameter.

Figure 4:
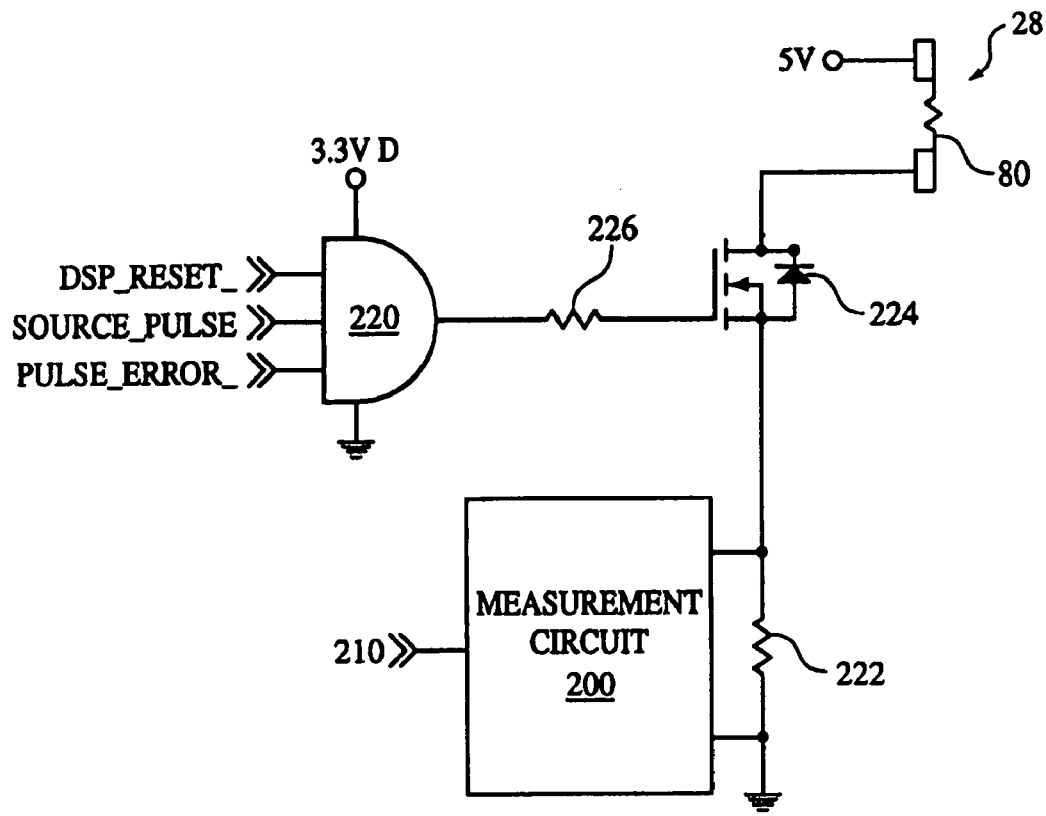
FIG. 4 is schematic diagram of a uni-polar electronic driver for use with the infrared radiation emitting element.

The present invention contemplates providing power to emitter 28 according to the above techniques using a unipolar or a bi-polar supply. FIG. 4 illustrates an exemplary embodiment of a source drive circuit with a single power supply of +5 VDC that is used to energize the emitter. As shown in this figure, an N-channel MOSFET 224 configured as a low-side switch provides the pulse to the emitter. A source pulse signal is provided to an AND gate 220. A current limiting resistor 226 serves to limit the maximum power that can be delivered to the low-side switch. A current sense resistor 222 is placed in the ground leg of the low-side switch transistor. The typical ON time for the emitter is 3500 microseconds with a period of 10 mS (which equates to a frequency of 100 Hz). The source emitter resistance (cold) can vary between 10 and 15 ohms. Measuring the voltage induced across sense resistor 222 with measurement circuit 200 permits a source current 210 to be determined. This signal is amplified and sampled by the analog to digital converter.

Figure 5:
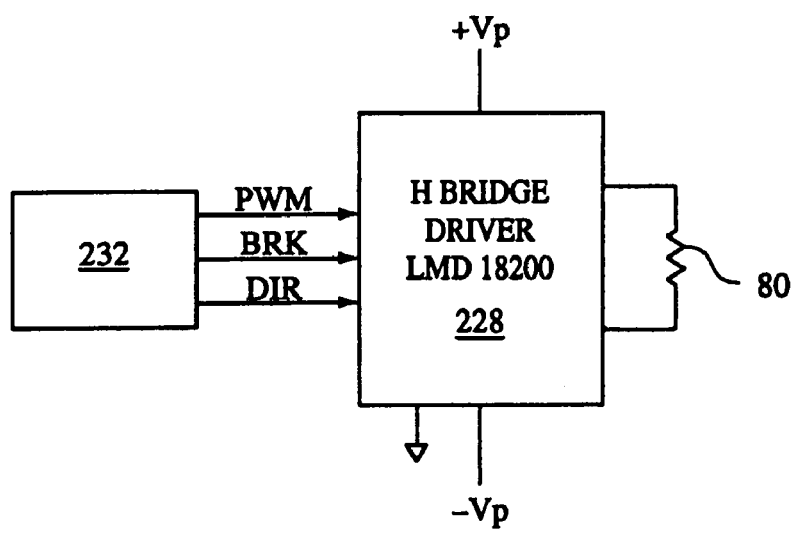
FIG. 5 is a schematic diagram of a bi-polar electronic driver for use with the infrared radiation emitting element.
Figure 6:
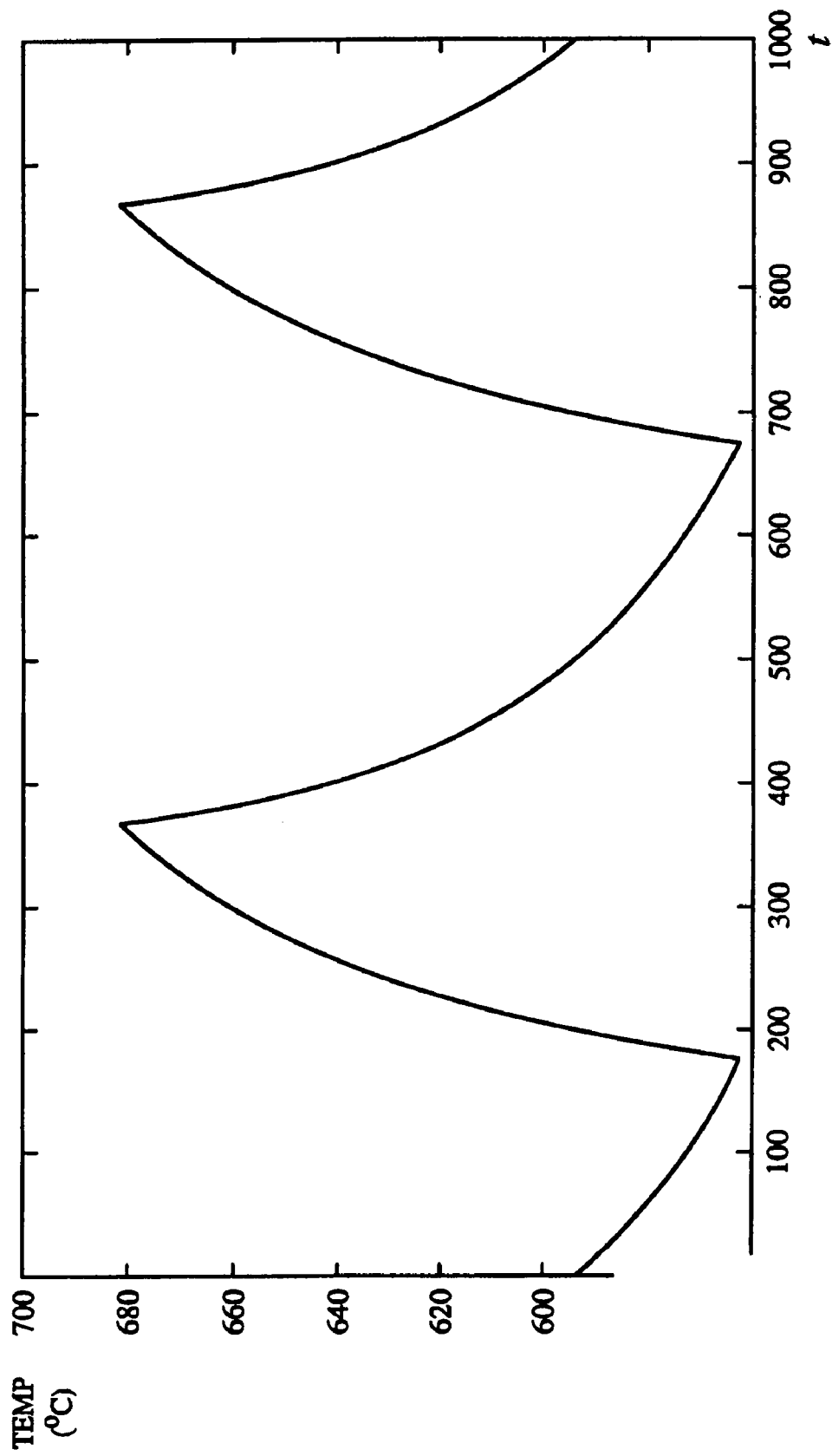
FIG. 6 is a plot depicting the thermal behavior of an infrared radiation emitting element over two cycles, with a peak temperature of 680° C.

Alternatively, FIG. 5 illustrates an exemplary embodiment of a source drive circuit 228 that uses a bipolar power supply of +/− Vp to control the operation of emitter 80. In the configuration shown, timing circuits 232 are controlled by a processor and provide timing signals to source drive circuit 228. A predetermined relationship between the emitter current and pulse width is determined during factory calibration, and the source current need not be measured during normal operation.

As the performance of an emitter is tied directly to the wave shape of the emitted energy, changes to resistance, changes to the applied emitter voltage or current, and timing. i.e., pulse width or duty cycle, effect its performance. The present invention contemplates using rectangular voltage or current pulses to power the infrared radiation emitting element because these pulse waveforms are relatively uncomplicated and yet quite effective in delivering power to the emitter. However, this invention is not limited to rectangular waveform voltage or current driving approaches.

A goal of the present invention to maintain the delivery of a constant power to the IR source under varying source voltage conditions. In this embodiment, each pulse provided to the IR source is substantially rectangular such that the delivered energy can be expressed using the definition of power and Ohms laws as:

$$E = \frac{V^2}{R} \times T, \tag{1}$$

where E is the energy delivered, V is the voltage across the infrared radiation source, R is the resistance of the infrared radiation source, and T is the pulse width (W in FIG. 7A) or on-time of the pulse. Similar derivations may be written for pulses that are not rectangular in shape. Solving for the infrared radiation source/emitter resistance yields:

$$R = \frac{V^2}{E} \times T. \tag{2}$$

The nature of infrared radiation sources (particularly those of the thick film type) yields a relationship such that the resistance of the source is dependent on the pulse width. Various mathematical relationships may be used to relate these two variables, but if a simple linear relationship is chosen, then the resistance R can be replaced with mT+k, where m is a slope and k an offset, and equation (2) is expressed as follows:

$$mt + k = \frac{V^2}{E} \times T. \quad (3)$$

Solving equation (3) for the pulse width yields:

$$T = \frac{K}{\frac{V^2}{E} - m}. \quad (4)$$

Figure 8:
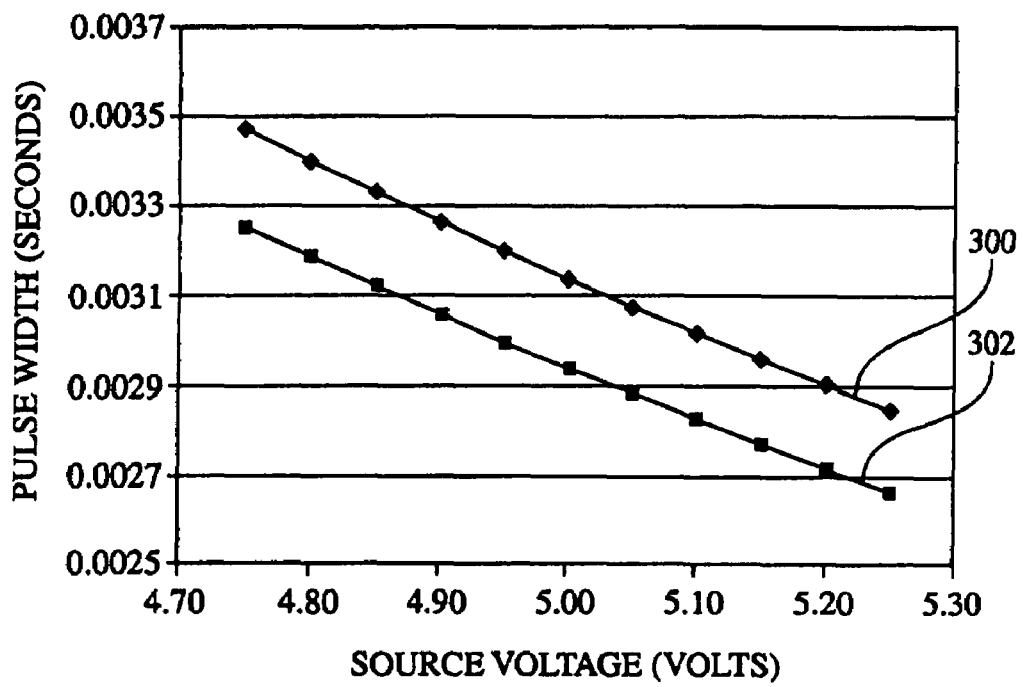
FIG. 8 is a chart showing a pulse width versus emitter voltage relationship for two different sensors.

A calibration procedure may be performed during the manufacturing/production process to establish a resistance to pulse width relationship for each source and key parameters of that relationship may be stored for later use during operation of the gas sensing system. FIG. 8 demonstrates two sensors with slightly different source characteristics and the resulting pulse width calculations. Line 300 represents a first sensor and line 302 represents the second sensor.

The present invention permits greater variances in the manufacturing and design processes for the emitter resistance and voltage than conventional methods while maintaining the performance specifications. The methods of the present invention also increase the stability of the gas measurements and extend the interval of accurate performance of the gas sensing system before re-calibration would be typically required. A further advantage of the present invention is that no additional voltage regulation is required, thus negating the need for additional complexity, cost, and power.

Figures 7A, 7B:
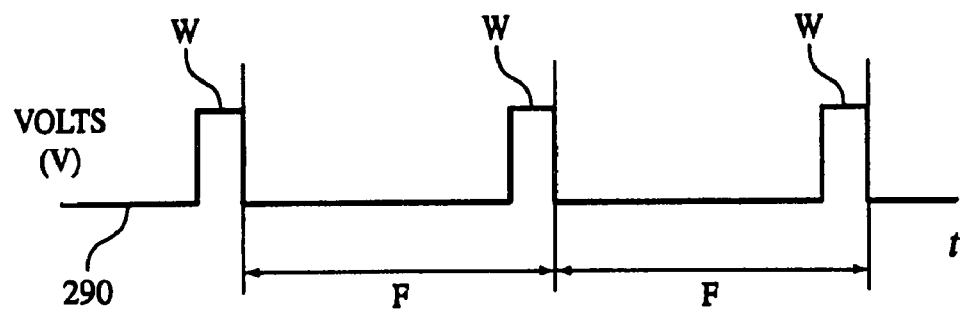
FIG. 7A is a waveform showing a series of pulses with a period of F.
FIG. 7B is a two-part table, where Part 1 illustrates the variation in peak temperature with a constant voltage but varying pulse width, and Part 2 illustrates the maintenance of a substantially constant peak temperature with ±5% variations in emitter voltage.
Figure 7C:
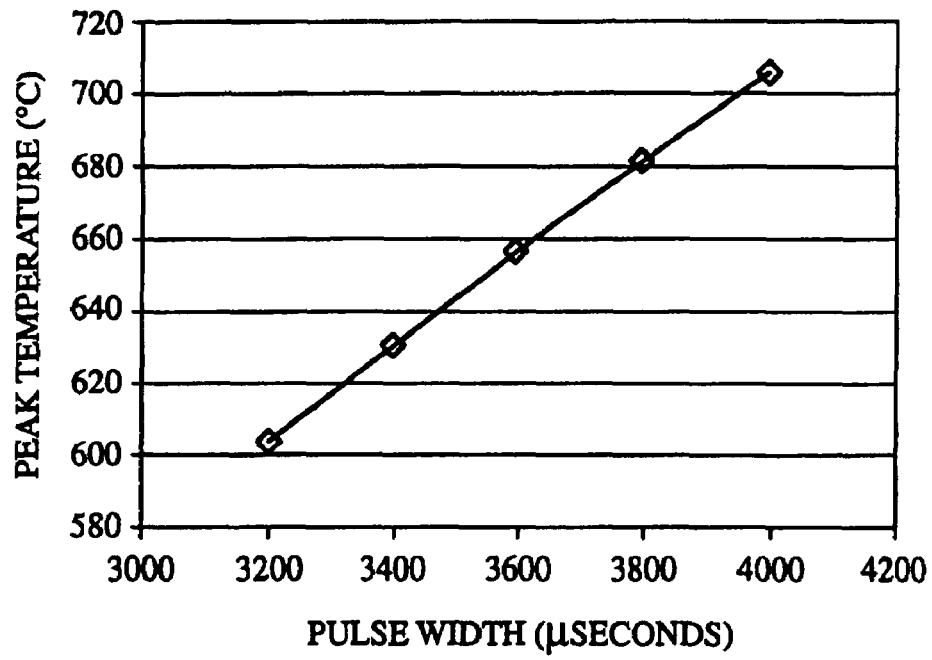
FIG. 7C is a plot of pulse width versus temperature with constant voltage.

Testing has shown that emitters have been successfully run with significant variations in voltage, while delivering apparently consistent modulated light output. The table in FIG. 7B provides test data illustrating the change in peak temperature with changes in source pulse width as well as the effectiveness of the present invention. A source voltage of 5 V, 250 mA with a duration (pulse width) of 3800 usec=0.0048 J/pulse, produces an equivalent peak source temperature @ 680° C. With conventional systems, if the source voltage were varied between 4.75 and 5.25 volts, the peak temperature modulation would vary between 110.4 and 125.5° C., a 15° C. change (FIG. 7B-Part 2). With the system of the present invention, if the specification allowed a 5% variation in the source voltage (i.e., emitter voltage) Vsrc, then a voltage of 5 volts could range between 4.75 to 5.25 volts, the pulse width would be appropriately varied and the peak modulation temperature would be maintained substantially constant (FIG. 7B-Part 1).

Figure 9:
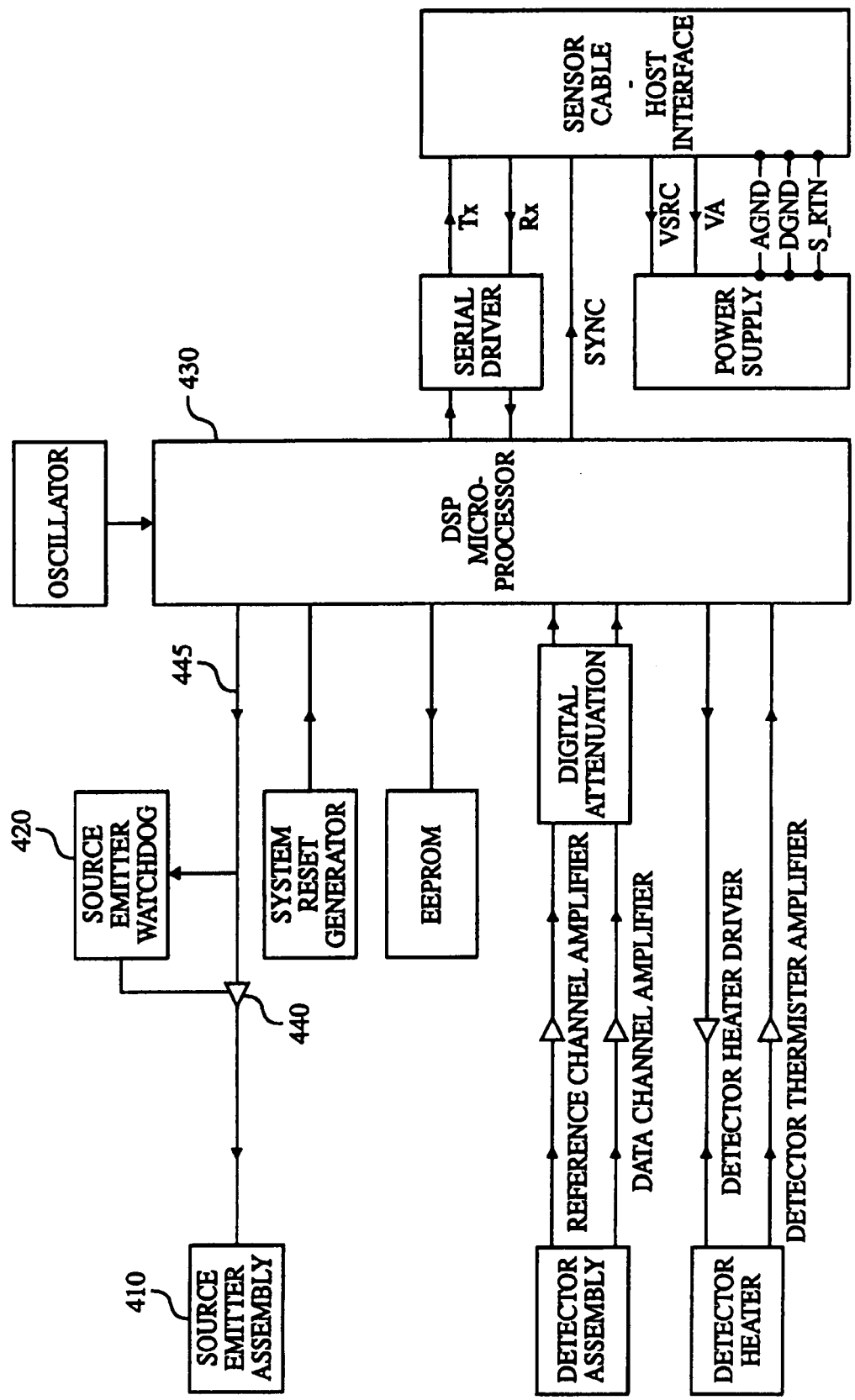
FIG. 9 is block diagram of a gas measurement system with a microprocessor controlled source drive according to the principles of the present invention.

The pulse timing may be generated by various means, including electrical circuitry as well as via a processor. FIG. 9 is a schematic diagram of a processor-based gas sensing system. Processor 430 generates a uni-polar pulse on line 445. A source emitter watchdog 420 provides a safety device to assure that the pulse is only passed to the source emitter assembly when a switch 440 is enabled. A current sensing circuit is used to measure the peak emitter current during each pulse. A voltage measurement circuit measures the peak voltage applied to the emitter during each pulse. The processor uses the voltage measurement to adjust the duration (width) of each pulse to maintain constant energy delivery. The current is used during the calibration process and can also be used to monitor and correct for emitter variations or changes over time to extend the usable life of the device without having to repeat the calibration process.

In the preferred embodiment as herein described, a rectangular voltage pulse is used to energize the infrared emitter, and the duration (width) of the pulse is varied in such a manner as to control the power delivered to the emitter. Alternatively, a periodic sinusoidal signal or a periodic signal of any shape may be used. The duration or shape of the energizing signal may be varied or adjusted based on measurements of one or more parameters as previously described herein in such a way as to control the power delivered to the emitter thereby maintaining constant power delivered to the emitter or constant infrared intensity radiated from the emitter.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of regulating infrared radiation output from an infrared radiation source comprising:
   applying a time-varying, periodic voltage signal to an infrared radiation source;
   measuring a parameter of the voltage signal; and
   adjusting the voltage signal to maintain a substantially constant delivered power to such an infrared radiation source, wherein adjusting the voltage signal is accomplished based on the measured parameter and a predetermined relationship between the measured parameter of the voltage signal and a resistance of such an infrared radiation source.

2. The method of claim 1, wherein the voltage signal is a uni-polar or a bi-polar voltage pulse.

3. The method of claim 1, wherein the parameter of the voltage signal is amplitude.

4. The method of claim 2, wherein adjusting the voltage signal includes adjusting a width of a voltage pulse in the voltage signal.

5. A method of regulating infrared radiation output from an infrared radiation source comprising:
   applying a voltage pulse to an infrared radiation source, wherein the voltage pulse has a duty cycle less than 100%;
   measuring a first parameter of the voltage pulse;
   measuring a second parameter of a current passing through the infrared radiation source resulting from the applying step; and
   adjusting the voltage pulse to maintain a substantially constant delivered power to the infrared radiation source based on the first parameter and the second parameter.

6. The method of claim 5, wherein the voltage pulse is a uni-polar or a bi-polar voltage.

7. The method of claim 5, wherein the parameter of the voltage pulse is amplitude.

8. The method of claim 5, wherein adjusting the voltage pulse includes adjusting a width of the voltage pulse.

9. A system for generating pulses of infrared radiation comprising:
- an infrared radiation source;
- a current sensor operatively coupled to the infrared radiation source so as to measure an electrical current passing through the infrared radiation source;
- a voltage sensor coupled to the infrared radiation source so as to measure an electrical voltage applied to the infrared radiation source; and
- means for applying electrical pulses to the infrared radiation source such that a substantially constant power is delivered to the infrared radiation source.

10. The system of claim 9, wherein the infrared radiation source comprises an emissive, electrically resistive material.

11. The system of claim 9, wherein the means for applying electrical pulses includes a uni-polar supply voltage.

12. The system of claim 11, wherein the voltage sensor measures the uni-polar supply voltage.

13. The system of claim 9, wherein the means for applying electrical pulses includes a bi-polar supply voltage.

14. The system of claim 13, where the voltage sensor measures the bi-polar supply voltage.

15. The system of claim 9, wherein the current sensor comprises a sense resistor and a measurement circuit to measure the voltage across the sense resistor.

* * * * *